US012734007B2

(12) United States Patent
Kim et al.

(10) Patent No.: US 12,734,007 B2
(45) Date of Patent: Sep. 15, 2026

(54) CART FOR OPTICAL COHERENCE TOMOGRAPHY

(71) Applicant: RAYWATT INC., Seoul (KR)

(72) Inventors: Joo Soo Kim, Seoul (KR); Dong Kwon Jang, Seoul (KR); Soon Won Jeong, Seoul (KR); Sang Won Woo, Seoul (KR); Jin Su Kim, Seoul (KR); Tae Sung Kim, Seoul (KR)

(73) Assignee: RAYWATT INC., Seoul (KR)

( * ) Notice: Subject to any disclaimer, the term of this patent is extended or adjusted under 35 U.S.C. 154(b) by 293 days.

(21) Appl. No.: 18/418,481

(22) Filed: Jan. 22, 2024

(65) Prior Publication Data

US 2025/0017678 A1 Jan. 16, 2025

(30) Foreign Application Priority Data

Jul. 14, 2023 (KR) ........................ 10-2023-0091849

(51) Int. Cl.
*A61B 50/13* (2016.01)
*A61B 5/00* (2006.01)

(52) U.S. Cl.
CPC ............ *A61B 50/13* (2016.02); *A61B 5/0066* (2013.01); *A61B 5/0084* (2013.01); *A61B 5/6852* (2013.01); *A61B 5/7445* (2013.01)

(58) Field of Classification Search
CPC ....... A61B 50/13; A61B 50/20; A61B 5/0066; A61B 5/0084; A61B 5/6852; A61B 5/7445; A61B 2560/0437
See application file for complete search history.

(56) References Cited

U.S. PATENT DOCUMENTS 6,246,905 B1 * 6/2001 Mogul .................. A61B 50/13 607/3
7,738,941 B2 * 6/2010 Hirota ................. A61B 5/0066 600/407
8,157,741 B2 * 4/2012 Hirota ..................... A61B 8/12 600/137

(Continued)

FOREIGN PATENT DOCUMENTS

| | | |
|---|---|---|
| CN | 108836277 A | 11/2018 |
| KR | 10-2023-0011255 A | 1/2023 |
| WO | 2012-158560 A2 | 11/2012 |

OTHER PUBLICATIONS

Cornaris P80. Lilac Garden. "Microlight Medical's multimodal cardiovascular OCT system was approved for marketing! Leading China's precision PCI into a new era of multimodality". (https://commercial.dxy.cn/article/803578, Dec. 13, 2021.).

(Continued)

*Primary Examiner* — Erez Gurari
(74) *Attorney, Agent, or Firm* — NKL Law; Jae Youn Kim

(57) ABSTRACT

According to an aspect of the present disclosure, a cart for optical coherence tomography includes a rotary catheter unit; a main body including a receiving member configured to receive the rotary catheter unit; a mobile unit coupled to a lower part of the main body and configured to move the main body on the ground; and a display unit connected to an upper part of the main body and configured to output information generated by the rotary catheter unit. Wherein the display unit is located inside at least two side surfaces of the main body.

13 Claims, 5 Drawing Sheets

(56) References Cited

U.S. PATENT DOCUMENTS

| | | | | |
|---|---|---|---|---|
| 8,951,224 | B2 * | 2/2015 | Wulfman | A61M 25/0147 604/95.01 |
| 9,168,003 | B2 * | 10/2015 | Suzuki | A61B 8/5207 |
| 9,326,793 | B2 * | 5/2016 | Alhumaid | A61B 17/3496 |
| 9,393,692 | B1 * | 7/2016 | Theobald | A61B 50/13 |
| 9,980,648 | B2 * | 5/2018 | Itoh | G01N 29/043 |
| 10,238,349 | B2 * | 3/2019 | Furuichi | A61B 5/743 |
| 10,271,818 | B2 * | 4/2019 | Kobayashi | A61B 5/7257 |
| 10,470,665 | B2 * | 11/2019 | Yamamoto | A61B 5/0073 |
| 10,705,014 | B2 * | 7/2020 | Sakamoto | A61B 1/00045 |
| 2005/0288571 | A1 * | 12/2005 | Perkins | A61B 5/0002 600/407 |
| 2007/0232893 | A1 * | 10/2007 | Tanioka | A61B 5/02007 600/407 |
| 2012/0253185 | A1 * | 10/2012 | Furuichi | A61B 8/4461 600/425 |
| 2014/0262553 | A1 * | 9/2014 | Pollock | B65F 1/1415 177/1 |
| 2015/0257651 | A1 * | 9/2015 | Angott | A61B 5/418 600/474 |
| 2016/0006992 | A1 * | 1/2016 | Roberts | H04N 23/63 348/113 |
| 2017/0065355 | A1 * | 3/2017 | Ross | A61B 34/30 |
| 2017/0071568 | A1 * | 3/2017 | Mitsuhashi | A61B 8/12 |
| 2017/0103363 | A1 * | 4/2017 | Boukhny | G16H 20/13 |
| 2017/0128136 | A1 * | 5/2017 | Post | A61B 34/30 |
| 2017/0184088 | A1 * | 6/2017 | Macari | F04B 43/1292 |
| 2017/0251990 | A1 * | 9/2017 | Kheradpir | A61B 50/13 |
| 2017/0316705 | A1 * | 11/2017 | Schultz | A61B 90/37 |
| 2018/0008498 | A1 * | 1/2018 | Sciacchitano | E05B 65/44 |
| 2018/0010366 | A1 * | 1/2018 | Sciacchitano | E05B 47/0001 |
| 2018/0168547 | A1 * | 6/2018 | Kim | A61B 50/33 |
| 2019/0290524 | A1 * | 9/2019 | Augustine | A61M 16/18 |
| 2021/0022821 | A1 * | 1/2021 | Chamorro | A61B 34/37 |
| 2021/0052212 | A1 * | 2/2021 | Yaroslavsky | A61B 5/0066 |
| 2021/0259796 | A1 * | 8/2021 | Danilkin | A61B 50/13 |
| 2022/0142621 | A1 * | 5/2022 | Zollinger | A61B 10/0096 |
| 2022/0218309 | A1 * | 7/2022 | Sakamoto | A61B 8/461 |
| 2023/0013321 | A1 * | 1/2023 | Horiike | A61B 1/00 |
| 2024/0065893 | A1 * | 2/2024 | Junger | A61F 9/00802 |
| 2024/0341782 | A1 * | 10/2024 | Kantor | A61M 5/1422 |
| 2025/0017678 | A1 * | 1/2025 | Kim | A61B 50/13 |
| 2025/0057429 | A1 * | 2/2025 | Ha | A61B 5/0084 |
| 2025/0331816 | A1 * | 10/2025 | Shiraishi | A61B 8/4427 |

OTHER PUBLICATIONS

Takashi Kubo, et al., “Optical coherence tomography imaging: current status and future perspectives: Current and future developments in OCT”, Cardiovasc Interv and Ther (2010) 25:2-10, Dec. 26, 2009, Japanese Association of Cardiovascular Intervention and Therapeutics.

* cited by examiner

CART FOR OPTICAL COHERENCE TOMOGRAPHY

CROSS-REFERENCE TO RELATED APPLICATION

This application claims the benefit under 35 USC 119 (a) of Korean Patent Applications No. 10-2023-0091849 filed on Jul. 14, 2023 in the Korean Intellectual Property Office, the entire disclosures of which are incorporated herein by reference for all purposes.

TECHNICAL FIELD

The present disclosure relates to a cart for optical coherence tomography which is equipped with a catheter device for performing optical coherence tomography (OCT) and configured to be movable.

BACKGROUND

Optical coherence tomography (OCT) is a non-invasive, contactless and high-resolution imaging technique based on light. In particular, OCT can be combined with a high-speed wavelength tuning technique and an optical endoscopic technique, which enables three-dimensional observation of interior walls of body vessels such as gastrointestinal tract, small intestine, bile duct, cardiac blood vessel, etc.

In general, a device for performing OCT needs to be equipped with a rotary junction coupled with a catheter, and electronic devices configured to control them and perform input and output operations, and may be configured as a cart or trolley further equipped with wheels that facilitate movement to a space where an operation is needed.

If the device for performing intravascular OCT is configured to be movable as described above, it is required to have rapid mobility, ease of use and safety in use in consideration of particularly an environment, space, or emergency situation where the device is to be used.

PRIOR ART DOCUMENT

Patent Document

Patent Document 1: Korean Patent Laid-open Publication No. 10-2023-0011255A (published on Jan. 20, 2023)

SUMMARY

In view of the foregoing, the present disclosure is conceived to provide a cart for optical coherence tomography which has stable weight distribution or balance so as to be stably movable. Also, the present disclosure is conceived to provide a cart for optical coherence tomography which is configured to ensure user convenience in use.

The problems to be solved by the present disclosure are not limited to the above-described problems. There may be other problems to be solved by the present disclosure.

According to an aspect of the present disclosure, a cart for optical coherence tomography includes a rotary catheter unit; a main body including a receiving member configured to receive the rotary catheter unit; a mobile unit coupled to a lower part of the main body and configured to move the main body on the ground; and a display unit connected to an upper part of the main body and configured to output information generated by the rotary catheter unit. Wherein the display unit is located inside at least two side surfaces of the main body.

According to another aspect of the present disclosure, a cart for optical coherence tomography includes a rotary catheter unit; a main body including a receiving member configured to receive the rotary catheter unit; a mobile unit coupled to a lower part of the main body and configured to move the main body on the ground; and a display unit connected to an upper part of the main body and configured to output information generated by the rotary catheter unit. Wherein in a top view of the cart for optical coherence tomography, the center of gravity of the display unit is located in an inner area of the main body.

The above-described aspects are provided by way of illustration only and should not be construed as liming the present disclosure. Besides the above-described embodiments, there may be additional embodiments described in the accompanying drawings and the detailed description.

According to the present disclosure, a cart for optical coherence tomography is configured such that the center of gravity of a display unit is located closer to a central axis of a main body, and, thus, a user can stably move the cart on the ground. In particular, if the cart for optical coherence tomography according to the present disclosure is operated in an emergency situation, the cart can keep its balance so as to avoid rollover accidents even when it moves fast.

Also, according to the present disclosure to the present disclosure, the cart is equipped with a grip portion of a manipulation unit at various heights and angles in various directions and thus can be rapidly and easily moved. Further, the cart is equipped with an input unit cradle at a different height from the grip portion and thus can be improved in convenience in use and can secure more space.

BRIEF DESCRIPTION OF THE DRAWINGS

Hereinafter, embodiments of the present disclosure will be described in detail with reference to the accompanying drawings so that the present disclosure may be readily implemented by a person with ordinary skill in the art. However, it is to be noted that the present disclosure is not limited to the embodiments but can be embodied in various other ways. In drawings, parts irrelevant to the description are omitted for the simplicity of explanation, and like reference numerals denote like parts through the whole document.

Through the whole document, the term “connected to” or “coupled to” that is used to designate a connection or coupling of one element to another element includes both a case that an element is “directly connected or coupled to” another element and a case that an element is “electronically connected or coupled to” another element via still another element. Further, through the whole document, the term “comprises or includes” and/or “comprising or including” used in the document means that one or more other components, steps, operation and/or existence or addition of elements are not excluded in addition to the described components, steps, operation and/or elements unless context dictates otherwise.

Through the whole document, the term “on” that is used to designate a position of one element with respect to another element includes both a case that the one element is adjacent to the other element and a case that any other element exists between these two elements.

Through the whole document, the term “unit” includes a unit implemented by hardware, a unit implemented by software, and a unit implemented by both of them. One unit may be implemented by two or more pieces of hardware, and two or more units may be implemented by one piece of hardware.

Through the whole document, a part of an operation or function described as being carried out by a terminal or device may be carried out by a server connected to the terminal or device. Likewise, a part of an operation or function described as being carried out by a server may be carried out by a terminal or device connected to the server.

Hereinafter, an embodiment of the present disclosure will be described in detail with reference to the accompanying drawings.

Figure 1:
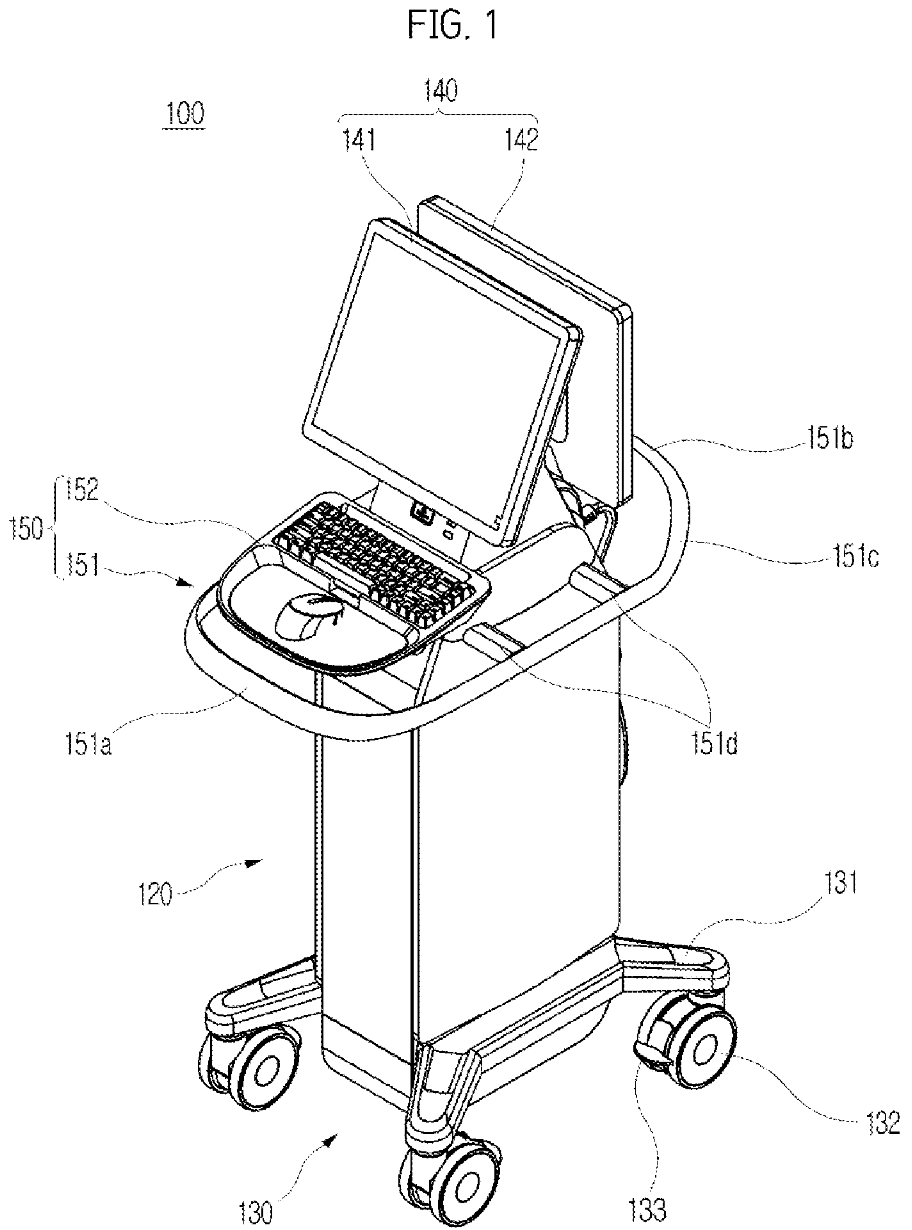

FIG. 1 is a perspective view of a cart for intravascular OCT according to an embodiment of the present disclosure.

Figure 2:
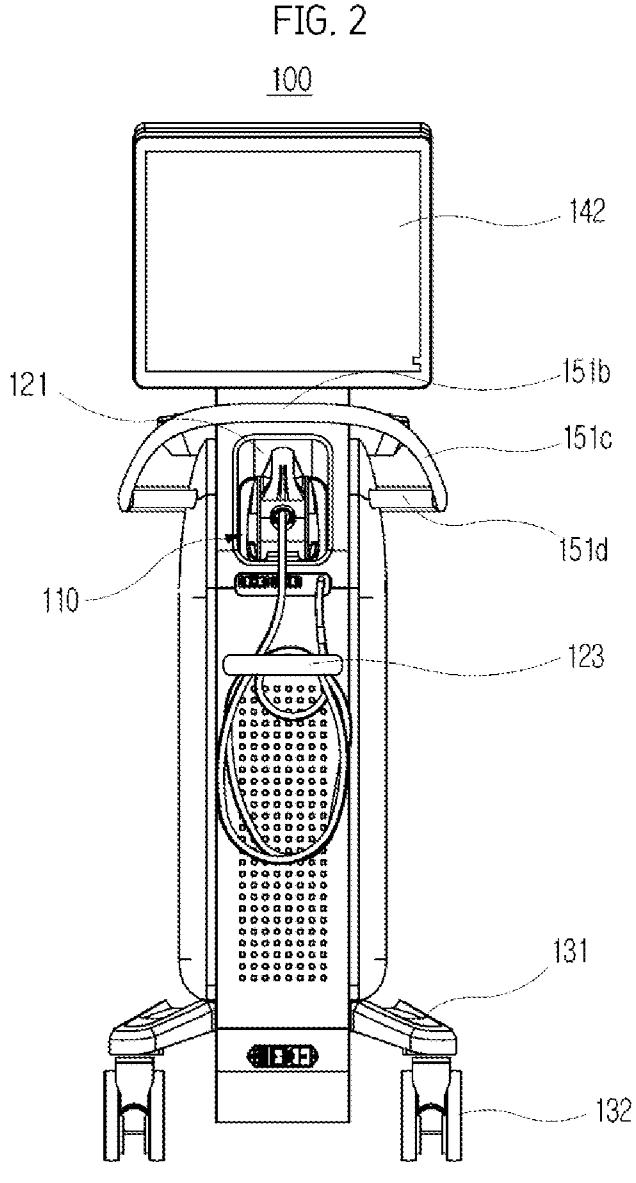

FIG. 2 is a rear view of the cart for intravascular OCT according to an embodiment of the present disclosure.

Figure 3:
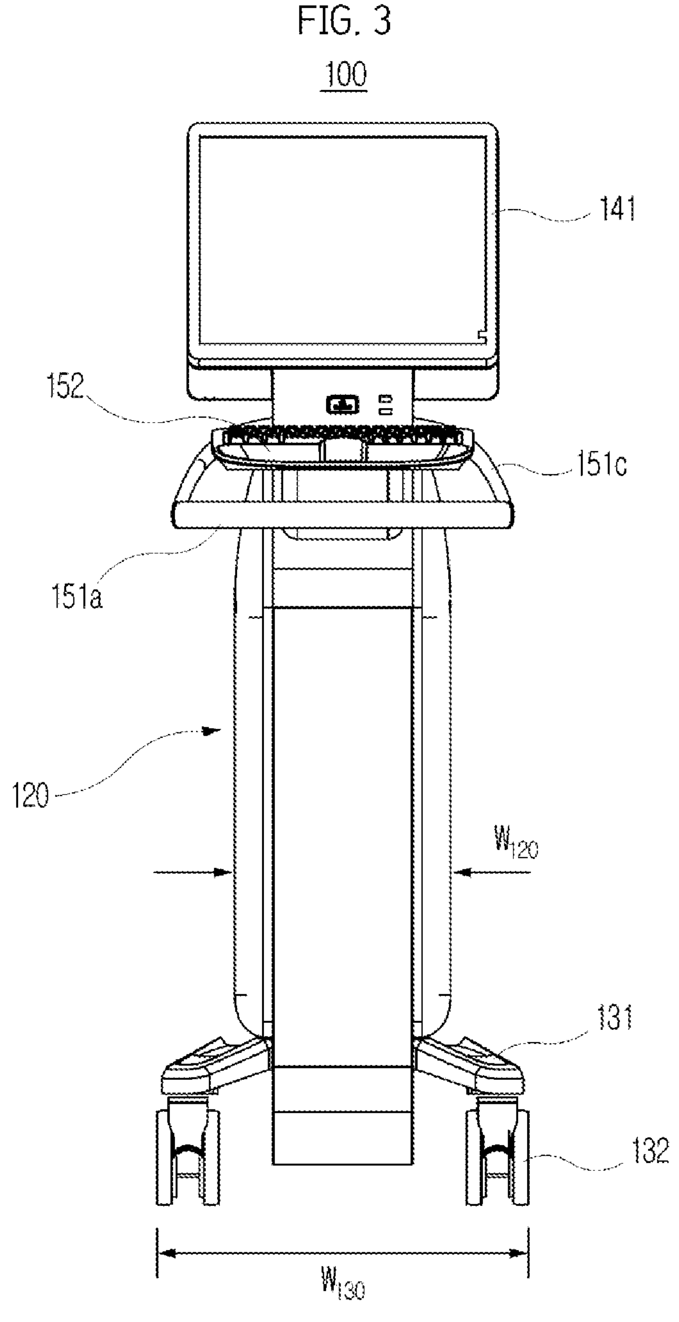

FIG. 3 is a front view of the cart for intravascular OCT according to an embodiment of the present disclosure.

Figure 4:
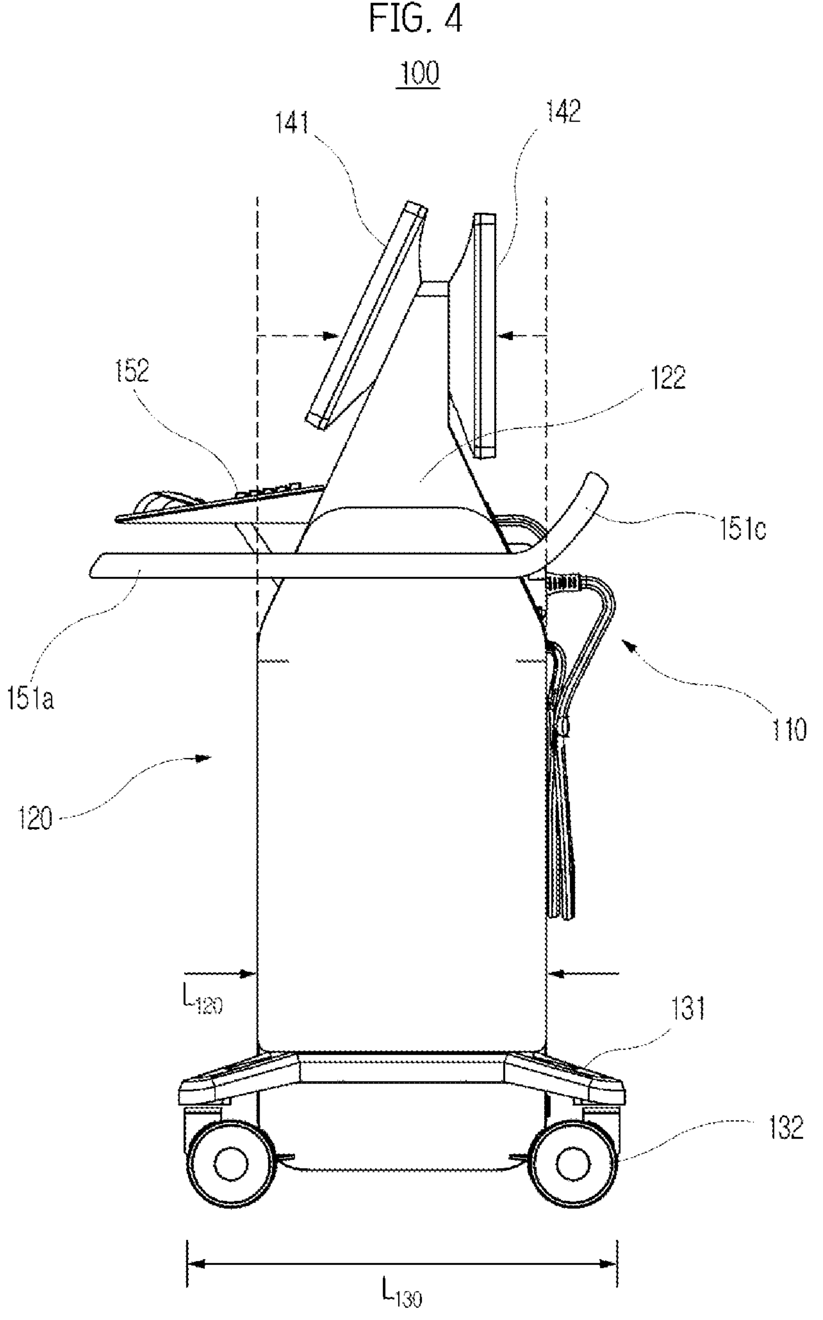

FIG. 4 is a side view of the cart for intravascular OCT according to an embodiment of the present disclosure.

Figure 5:
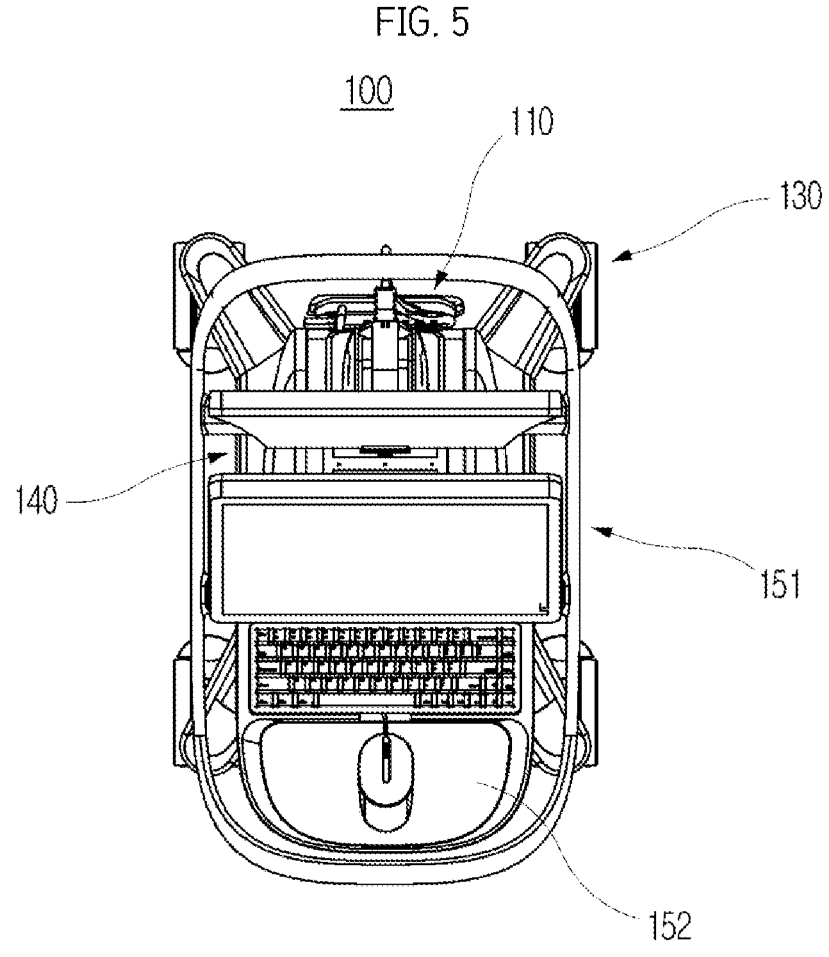

FIG. 5 is a plan view of the cart for intravascular OCT according to an embodiment of the present disclosure.

DETAILED DESCRIPTION

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Through the whole document, the term “connected to” or “coupled to” that is used to designate a connection or coupling of one element to another element includes both a case that an element is “directly connected or coupled to” another element and a case that an element is “electronically connected or coupled to” another element via still another element. Further, it is to be understood that the term “comprises or includes” and/or “comprising or including” used in the document means that one or more other components, steps, operation and/or existence or addition of elements are not excluded in addition to the described components, steps, operation and/or elements unless context dictates otherwise and is not intended to preclude the possibility that one or more other features, numbers, steps, operations, components, parts, or combinations thereof may exist or may be added.

Through the whole document, the term “on” that is used to designate a position of one element with respect to another element includes both a case that the one element is adjacent to the other element and a case that any other element exists between these two elements.

Through the whole document, the term “unit” includes a unit implemented by hardware, a unit implemented by software, and a unit implemented by both of them. One unit may be implemented by two or more pieces of hardware, and two or more units may be implemented by one piece of hardware.

Through the whole document, a part of an operation or function described as being carried out by a terminal or device may be carried out by a server connected to the terminal or device. Likewise, a part of an operation or function described as being carried out by a server may be carried out by a terminal or device connected to the server.

Hereinafter, the present disclosure will be explained in detail with reference to the accompanying configuration views or process flowcharts.

FIG. 1 is a perspective view of a cart for intravascular OCT according to an embodiment of the present disclosure. FIG. 2 is a rear view of the cart for intravascular OCT according to an embodiment of the present disclosure. FIG. 3 is a front view of the cart for intravascular OCT according to an embodiment of the present disclosure. FIG. 4 is a side view of the cart for intravascular OCT according to an embodiment of the present disclosure. FIG. 5 is a plan view of the cart for intravascular OCT according to an embodiment of the present disclosure.

Referring to FIG. 1 to FIG. 3, a cart for intravascular OCT 100 according to an embodiment of the present disclosure may include a rotary catheter unit 110, a main body 120, a mobile unit 130, a display unit 140, and a manipulation unit 150.

The rotary catheter unit 110 may include a catheter to be inserted into a body for intravascular OCT, and a rotary junction module configured to rotate or insert the mounted catheter. The rotary catheter unit 110 may be connected to the main body 120 through a cable as shown in FIG. 2.

The main body 120 may have a longitudinally extending shape, and may have an approximately cuboid shape. In the present embodiment, one side surface and the other side surface each having a narrow width may serve as front and rear surfaces, and both surfaces each having a wide width may serve as left and right side surfaces.

As shown in FIG. 2, the main body 120 may be equipped with a receiving member 121. The receiving member 121 may be a groove recessed inwards from one surface (rear surface) of the main body 120. At least a part of the rotary catheter unit 110 is inserted into the receiving member 121 and thus can be received or cradled by the receiving member 121.

The mobile unit 130 may be provided at a lower part of the main body 120. The mobile unit 130 may be configured to move the cart for intravascular OCT 100 including the main body 120 on the ground.

The display unit 140 serves to output information to a user, and is connected to an upper part of the main body 120 and configured to output information generated by the rotary catheter unit 110 or control information for manipulating the device.

The display unit 140 according to the present embodiment may be located such that the cart for intravascular OCT 100 can be stably and rapidly moved.

Specifically, the display unit 140 may be located inside at least the two side surfaces of the main body 120. For example, in the present embodiment, the display unit 140 may be spaced inwards from the front and rear surfaces of the main body 120 as shown in FIG. 4.

Also, in the present embodiment, the center of gravity of the display unit 140 may be located as near a central portion of the main body 120 as possible. When viewed from above the cart for intravascular OCT 100 of the present disclosure as shown in FIG. 5, i.e., in a top view of the cart for intravascular OCT 100, the center of gravity of the display unit 140 may be located in an inner area of the main body 120.

In the cart for intravascular OCT 100 according to the present disclosure, the display unit 140 at an upper part is located close to a central axis of the main body 120, and, thus, the user can rapidly and stably move the cart for intravascular OCT 100 on the ground. In particular, if the cart for intravascular OCT 100 according to the present disclosure is operated in an emergency situation, it is possible to avoid time delay or rollover accidents.

The display unit 140 of the present embodiment may include a first display 141 and a second display 142. Referring to FIG. 1 and FIG. 4, the first display 141 may be located to face the front surface of the main body 120 and located inside one side surface of the main body 120. Further, the second display 142 may be located to face the rear surface of the main body 120 and located inside the other side surface of the main body 120. The first display 141 and the second display 142 may be located to face away from each other.

Meanwhile, in the present embodiment, the main body 120 may further include an inclined portion 122 and thus can help stably place the display unit 140 and improve user convenience.

The inclined portion 122 may have an upwardly extending shape inclined from the one side surface and the other side surface of the main body 120 in a direction facing each other. As shown in FIG. 4, the inclined portion 122 may have an inclined surface facing a front upper surface and an inclined surface facing a rear upper surface.

The receiving member 121 of the main body 120 may be provided in the inclined portion 122. As shown in FIG. 4, the receiving member 121 may be provided on the inclined surface facing the rear upper surface and is upwardly open. Thus, the user can easily check the inside of the receiving member 121 and easily insert and remove the rotary catheter unit 110.

Also, the first display 141 may be provided on one side surface of the inclined portion 122 facing a front upper side. Therefore, the first display 141 may be located at the front to face upwards at a predetermined angle. Due to the placement of the first display 141, it is easy for an operator who stands in front of the cart for intravascular OCT 100 according to the present disclosure and manipulates the cart for intravascular OCT 100 to check the first display 141.

Further, the second display 142 may be provided at an upper part of the inclined portion 122 to be in parallel with the other side surface of the main body 120 facing a rear side. Therefore, the second display 142 may be provided to make it easy to check information on the other side surface of the cart for intravascular OCT 100 according to the present disclosure.

As shown in FIG. 2, a cable bracket 123 may be provided at a lower portion of the receiving member 121 provided in the inclined portion 122. The cable bracket 123 can suppress the occurrence of unwanted departure or interference of a cable in an emergency situation.

Hereinafter, a configuration of the mobile unit 130 according to the present embodiment will be described.

As shown in the drawings, the mobile unit 130 of the present embodiment may include a leg portion 131 and a roller portion 132. The leg portion 131 may extend to protrude to the outside of the main body 120, and the roller portion 132 may be coupled to an end portion of the leg portion 131 and its central axis may be fixed. Thus, the roller portion 132 can roll on the ground.

The mobile unit 130 including the leg portion 131 and the roller portion 132 may protrude to the outside from four side surfaces of the main body 120 to land on the ground. As shown in FIG. 1 and FIG. 5, the leg portion 131 may extend to the outside in a diagonal direction from four lower corners of the main body 120, and the roller portion 132 may be connected to a lower portion of the leg portion 131 so as to land on the ground.

As shown in FIG. 3 and FIG. 4, a width W130 of the mobile unit 130 may be greater than a width W120 of the main body 120, and a length L130 of the mobile unit 130 may be greater than a length L120 of the main body 120. In a top view, landing points of the roller portion 132 may be located in an outer area of the main body 120.

As described above, the mobile unit 130 is provided outside the side surfaces of the main body 120, and, thus, the cart for intravascular OCT 100 according to the present disclosure can stably move on the ground. Also, the mobile unit 130 moves while occupying a greater space on the ground than the main body 120, and, thus, the main body 120 and the display unit 140 can be supported in a structurally safe manner.

The mobile unit 130 of the present embodiment may further include a roller fixing portion 133 provided in the roller portion 132 and configured to allow or restrict rotation of the roller portion 132.

Hereinafter, the manipulation unit 150 according to the present embodiment will be described.

The manipulation unit 150 may include a grip portion 151 and an input unit cradle 152. The grip portion 151 may be provided in order for the user to move the cart for intravascular OCT 100 according to the present disclosure with force. Also, the input unit cradle 152 may provide an input unit for control input, such as a keyboard or a mouse, at a position that is convenient for use.

The grip portion 151 may be provided to protrude to the outside from at least one side surface of the main body 120. As can be seen from FIG. 5, the grip portion 151 of the present embodiment is spaced apart from the main body 120 so as to surround the main body 120. Thus, the user can easily hold the grip portion 151 from all side directions. Also, as can be seen from FIG. 2 to FIG. 4, the grip portion 151 of the present embodiment may be provided at a height equal to that of the inclined portion 122, i.e., at an average height for easy access of the user.

More specifically, the grip portion 151 may include a first cross bar 151*a*, a second cross bar 151*b*, a cross connection bar 151*c*, and a main body connection bar 151*d*.

The first cross bar 151*a* may extend at a predetermined height in a transverse direction. Further, the second cross bar 151*b* may extend at a different height from the first cross bar 151*a* in the transverse direction. The first cross bar 151*a* and the second cross bar 151*b* are spaced apart from the side surfaces of the main body 120, and, thus, the user can easily hold the cross bars.

In the present embodiment, the first cross bar 151*a* may be located at a lower height than the second cross bar 151*b*. Also, the first cross bar 151*a* may extend to surround the front surface and the left and right side surfaces of the main body 120, and the second cross bar 151*b* may extend to be spaced apart from the rear surface of the main body 120. The second cross bar 151*b* may be located on the rear surface of the main body 120 at a higher height than the first cross bar 151*a*, and the receiving member 121 may be located under the second cross bar 151*b*.

The cross connection bar 151*c* may be configured to connect the first cross bar 151*a* to the second cross bar 151*b*. The cross connection bar 151*c* may extend diagonally to connect two points at different heights, and may serve as a grip, which is more convenient to the user, depending on the circumstances. Further, the second cross bar 151*b* and the receiving member 121 are located at different heights so as not to overlap each other, which is helpful in quick storage and movement.

The main body connection bar 151*d* may extend from the first cross bar 151*a*, the second cross bar 151*b* or the cross connection bar 151*c* to be supported by the side surface of the main body 120. The main body connection bar 151*d* may be supported at a height equal to that of the inclined portion 122 of the main body 120. Since the main body connection bar 151*d* extends to an appropriate distance from the main body 120, the entire grip portion 151 may be spaced apart at an appropriate distance from the main body 120.

The input unit cradle 152 may be spaced apart from the grip portion 151. The input unit cradle 152 may be provided around the inclined portion 122 of the main body 120. In the present embodiment, the input unit cradle 152 may be provided on the front surface of the main body 120 and under the first display 141.

Also, the input unit cradle 152 of the present embodiment is provided above the grip portion 151, and the input unit cradle 152 and the grip portion 151 are located at different heights from each other. Therefore, the manipulation unit 150 can occupy a smaller space overall in a lateral direction, and, thus, it is possible to suppress a structural enlargement of the device in the lateral direction.

The above description of the present disclosure is provided for the purpose of illustration, and it would be understood by a person with ordinary skill in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

EXPLANATION OF CODES

100: Cart for intravascular OCT
110: Rotary catheter unit
120: Main body
121: Receiving member
122: Inclined portion
123: Cable bracket
130: Mobile unit
131: Leg portion
132: Roller portion
133: Roller fixing portion
140: Display unit
141: First display
142: Second display
150: Manipulation unit
151: Grip portion
151*a*: First cross bar
151*b*: Second cross bar
151*c*: Cross connection bar
151*d*: Main body connection bar
152: Input unit cradle

We claim:

1. A cart for optical coherence tomography, comprising:
a rotary catheter unit;
a main body including a receiving member configured to receive the rotary catheter unit, at least two side surfaces, and an inclined portion having an upwardly extending shape inclined from a first one of the at least two side surfaces and a second one of the at least two side surfaces in a direction facing each other;
a mobile unit coupled to a lower part of the main body and configured to move the main body on the ground; and
a display unit connected to an upper part of the main body and configured to output information generated by the rotary catheter unit, and
wherein the receiving member is disposed on the inclined portion.

2. The cart for optical coherence tomography of claim 1, wherein the display unit includes:
a first display spaced inward from the first one of the at least two side surfaces of the main body; and
a second display spaced inward from a rear surface of the main body.

3. A cart for optical coherence tomography, comprising:
a rotary catheter unit;
a main body including a receiving member configured to receive the rotary catheter unit, at least two side surfaces, and an inclined portion having an upwardly extending shape inclined from a first one of the at least two side surfaces and a second one of the at least two side surfaces in a direction facing each other;
a mobile unit coupled to a lower part of the main body and configured to move the main body on the ground; and
a display unit connected to an upper part of the main body and configured to output information generated by the rotary catheter unit,
wherein the display unit includes a first display disposed on one side surface of the inclined portion and a second display disposed on another side surface of the inclined portion.

4. The cart for optical coherence tomography of claim 3, wherein the second display is provided in parallel with the second one of the at least two side surfaces of the main body.

5. The cart for optical coherence tomography of claim 1, wherein the mobile unit includes:
a leg portion extending to protrude to the outside of the main body; and
a roller portion coupled to an end portion of the leg portion and roll on the ground.

6. The cart for optical coherence tomography of claim 1, wherein the at least two side surfaces comprises four side surfaces, and
wherein the mobile unit protrudes to the outside from the four side surfaces of the main body to land on the ground.

7. The cart for optical coherence tomography of claim 1, further comprising:
a manipulation unit including a grip portion protruding to the outside from the at least two side surfaces of the main body.

8. A cart for optical coherence tomography, comprising:
a rotary catheter unit;
a main body including a receiving member configured to receive the rotary catheter unit;
a mobile unit coupled to a lower part of the main body and configured to move the main body on the ground;

a display unit connected to an upper part of the main body and configured to output information generated by the rotary catheter unit; and a manipulation unit including a grip portion protruding to the outside from one of at least two side surfaces of the main body, wherein the grip portion includes:

a first cross bar extending at a predetermined height to be spaced apart from the main body; and a second cross bar extending at a different height from the first cross bar to be spaced apart from the main body.

9. The cart for optical coherence tomography of claim 8, wherein the grip portion further includes:

a cross connection bar whose both end portions are connected to the first cross bar and the second cross bar, respectively; and a main body connection bar extending from the first cross bar, the second cross bar or the cross connection bar to be supported by one of the at least two side surfaces of the main body.

10. The cart for optical coherence tomography of claim 7, wherein the manipulation unit further includes:

an input unit cradle spaced apart from the grip portion and provided on one of the at least two side surfaces of the main body to cradle an input unit.

11. The cart for optical coherence tomography of claim 7, wherein the manipulation unit is provided around the inclined portion.

12. The cart for optical coherence tomography of claim 7, wherein the grip portion includes:

a first cross bar extending at a predetermined height to be spaced apart from the first one of the at least two side surfaces of the main body; and a second cross bar extending at a higher height than the first cross bar to be spaced apart from the second one of the at least two side surfaces of the main body, and wherein the receiving member is located under the second cross bar.

13. A cart for optical coherence tomography, comprising:

a rotary catheter unit;

a main body including a receiving member configured to receive the rotary catheter unit, and an inclined portion having an upwardly extending shape inclined from a first side surface and a second side surface in a direction facing each other;

a mobile unit coupled to a lower part of the main body and configured to move the main body on the ground; and a display unit connected to an upper part of the main body and configured to output information generated by the rotary catheter unit, wherein in a top view of the cart for optical coherence tomography, the center of gravity of the display unit is located in an inner area of the main body, and wherein the display unit includes a first display disposed on the first side surface of the inclined portion and a second display disposed on the second side surface of the inclined portion.

* * * * *